United States Patent [19]

Nallapareddy

[11] Patent Number: 5,120,318
[45] Date of Patent: Jun. 9, 1992

[54] ARTHROSCOPY PORTAL MAKER

[76] Inventor: Harinathareddy Nallapareddy, 3040 Lawrence Crescent, Flossmoor, Ill. 60422

[21] Appl. No.: 543,332

[22] Filed: Jun. 25, 1990

[51] Int. Cl.⁵ .............................................. A61M 5/178
[52] U.S. Cl. ........................................ 604/164; 604/165
[58] Field of Search .............. 604/158, 161, 164, 167, 604/170, 165, 264, 51

[56] References Cited

U.S. PATENT DOCUMENTS

| | | | |
|---|---|---|---|
| 3,406,685 | 10/1968 | May | 128/214.4 |
| 3,844,272 | 10/1974 | Banko | 128/2 B |
| 3,994,287 | 11/1976 | Turp | 128/6 |
| 4,414,974 | 11/1983 | Dotson et al. | 128/305 |
| 4,491,132 | 1/1985 | Aikins | 128/305 |
| 4,512,344 | 4/1985 | Barber | 128/305 |
| 4,580,563 | 4/1986 | Gross | 128/305 |
| 4,609,370 | 9/1986 | Morrison | 604/165 |
| 4,649,919 | 3/1987 | Thimsen et al. | 128/305 |
| 4,696,308 | 9/1987 | Meller et al. | 128/754 |
| 4,723,546 | 2/1988 | Zagorski | 128/305 |
| 4,817,631 | 4/1989 | Schnepp-Pesch et al | 604/167 |
| 4,834,729 | 5/1989 | Sjostrom | 128/318 |
| 4,986,814 | 1/1991 | Burney et al. | 604/164 |
| 5,007,902 | 4/1991 | Witt | 604/164 |

Primary Examiner—Gene Mancene
Assistant Examiner—Michael Lynch
Attorney, Agent, or Firm—Dick and Harris

[57] ABSTRACT

An arthroscopy portal maker which facilitates substantially precise insertion and location of each of the surgical tools necessary to make a portal, within the area where further arthroscopic surgical procedures are to be performed. The device comprises a canulated shaft which has a cutting end and a gripping portion proximate the end opposite the cutting end. The internal channel of the canulated shaft facilitates slidable cooperation with a puncturing tool, and then a blunt wire rod, which is slidably interchanged with the puncturing tool. After the portal is made, the canulated shaft having a cutting end, is slidably removed over the blunt wire rod, and a conventional canula is then slidably inserted thereover, through the portal and to the location previously occupied by the canulated shaft having a cutting end. The blunt wire rod is then removed so as to enable further surgical procedures to be performed at substantially the precise location previously occupied by the puncturing tool and the blunt wire rod.

3 Claims, 4 Drawing Sheets

ARTHROSCOPY PORTAL MAKER

BACKGROUND OF THE INVENTION

The present invention relates in general to surgical devices, and, in particular, to an arthroscopy portal maker, and a method for using same, for use in arthroscopic procedures. The present invention is constructed with a canulated shaft which has a cutting end and a gripping portion located near the end opposite the cutting end of the shaft. The shaft further comprises an internal channel which slidably cooperates over and around a puncturing tool, such as a conventional spinal needle, and then a blunt wire rod, among other things, which is slidably interchanged with the puncturing tool.

Arthrocopic surgery is a procedure which enables surgery to be performed within the confines of an anatomical joint, such as the knee joint or shoulder joint, without the necessity of making large incisions, or the need to widely expose the area where the surgery is to be performed. Prior to actually performing the surgical procedures within the joint itself, a portal must be made which facilitates insertion of additional arthroscopic tools. Typically, such portals are made by first positioning a spinal needle at the point where the portal is to be made and then forcing the spinal needle toward the joint so as to puncture the skin. The surgeon then continues forcing the spinal needle through the tissue below the skin until the tip of the spinal needle is located where further arthroscopic surgical procedures are to be performed.

After the spinal needle has been properly inserted, the surgeon then removes the needle from the joint, and replaces it with a canula/obturator or canula/trocar assembly. This canula/obturator or canula/trocar assembly is forced through the hole made by the spinal needle, under the theory that it will follow approximately the same path as that previously occupied by the spinal needle, until the end of the canula/obturator or canula/trocar assembly is substantially positoned within the joint area. Once inserted, the obturator or trocar is then slidably removed from the canula so as to enable additional surgical tools to be slidably inserted through the remaining canula so as to enable further surgical procedures to be performed.

While such methods of making portals have been successful, few if any of such prior art procedures, or the prior art devices used to perform such procedures, effectively facilitate locating a canula within the joint area through slidable guided cooperation with a puncturing tool, such as a spinal needle. As one of the primary objectives of arthroscopic surgery is to minimize the size, as well as the number, of cuts to the area where the surgery is being performed (for purposes of reducing trauma and accordingly the amount of time necessary for healing), it is highly desirous that a portal be made with minimal amount of damage to the tissue. Furthermore, few, if any prior art methods and devices utilize a canulated shaft which has a cutting end, for use in slidable cooperation with a puncturing tool, as well as a blunt wire rod which is slidably interchanged with the puncturing tool, during the procedure to make the portal, for the specific purpose of minimizing damage to tissue while making the portal, and accordingly, for ensuring that each surgical tool inserted through the portal is positioned at substantially the precise location as the previously used surgical tool.

It is thus an object of the present invention to provide an arthroscopy portal maker which reduces the risk of trauma to the patient, as well as the healing process, by eliminating the risk of excessive cutting to the tissue during the making of the portal, as well as after the portal has been made.

It is additionally an object of the present invention to provide an arthroscopy portal maker which facilitates the slidable interchangeability with additional surgical instruments, while at the same time ensuring that each instrument will be positioned in substantially the same location as that occupied by the previous instrument.

It is still further an object of the present invention to provide an arthroscopy portal maker which comprises a canulated shaft having a cutting end and a gripping end opposite the cutting end, for insertion of the cutting end into the joint area where further surgical procedures are to be performed.

These and other objects of the present invention shall become apparent from the following description of the drawings and claims that follow.

SUMMARY OF THE INVENTION

The present invention relates to an arthroscopy portal maker which includes means for puncturing, wherein the puncturing means has a substantially sharp end and a shank portion, and a canulated shaft. The canulated shaft has a first end and a second end which is opposite to the first end, and further includes a cutting means located at the first end as well as an internal channel running through the longitudinal axis of the shaft itself. The canulated shaft is removably and slidably engaged over at least a portion of the puncturing means. When slidably engaged, the cutting means of the canulated shaft is positioned near the substantially sharp end of the puncturing means.

In the preferred embodiment of the invention, the internal channel of the canulated shaft is substantially cylindrical in shape. Furthermore, this internal channel ideally has an inner diameter which is slightly larger than the outer diameter of the puncturing means. In this embodiment, the puncturing means comprises a spinal needle.

In another embodiment of the invention, the arthroscopy portal maker further includes a rod for slidable interchangeability with the puncturing means after a puncture has actually been made. Preferably, this rod comprises an 18 gauge sterilized wire. Accordingly, it is also preferred that the internal channel of the canulated shaft has an inner diameter which is slightly larger than the outer diameter of the rod.

In yet another embodiment of the invention, the arthroscopy portal maker further comprises an obturator which has a longitudinal axis. This obturator slidably engages with the internal channel of the canulated shaft. Additionally, the obturator itself includes an internal channel which thereby facilitates slidable engagement over and around the rod. The internal channel of the obturator spans the obturator's entire longitudinal axis.

In the preferred embodiment of the invention, the canulated shaft comprises preclusion means which serve to eliminate over insertion of the canulated shaft into a joint area. Such preclusion means comprise one or more protrusions which extend from the gripping portion of the canulated shaft.

In one embodiment of the invention, the preclusion means further include at least a portion of the canulated shaft, which is closest to the second end of the shaft itself, having an outer diameter which is greater than the outer diameter of at least a portion of the canulated shaft closest to the cutting means.

The present invention also relates to a method for making a portal for arthroscopic surgery. This method comprises the steps of slidably positioning a canulated shaft, which has a cutting portion and gripping portion, over a puncturing tool of the type having a first sharp end and second end, so as to locate the cutting portion of the canulated shaft near the first sharp end of the puncturing tool. The sharp end of the puncturing tool is then located where the portal is intended to be made. Once in proper position, a puncture is made where the portal is to be made. After the puncture has been made, the puncturing tool is forced through the puncture to an area where further surgical procedures are to be performed. After the puncturing tool has been properly inserted, the canulated shaft is slid along the shaft of the puncturing tool so that the cutting end of the canulated shaft is headed towards the puncture itself. The cutting end of the canulated shaft is then pushed through the skin toward the sharp end of the puncturing tool until it is properly positioned within the joint area. After the canulated shaft has been inserted, the puncturing tool is slidably removed from the canulated shaft, and accordingly from within the joint area. A rod is then slidably inserted through the canulated shaft and through the puncture caused by the puncturing tool. Next, the canulated shaft is withdrawn from within the joint area by slidably removing it from over the rod. Once the canulated shaft is removed, a hollow tube, such as a conventional canula, is then positioned over and around the rod and slid into the position within the joint area which had been previously occupied by the canulated shaft. The rod is then slidably removed from the hollow tube, and accordingly out and away from the area where further surgical procedures are to be performed.

The preferred method further includes the step of slidably inserting the rod through the canulated shaft and through the puncture caused by the puncturing tool, and then additionally slidably inserting the rod to substantially the precise location where the puncturing tool had previously occupied.

An additional method includes a step of slidably inserting a canulated obturator into the hollow tube, prior to the step of slidably inserting a hollow tube over and around the rod.

DETAILED DESCRIPTION

Figure 1:
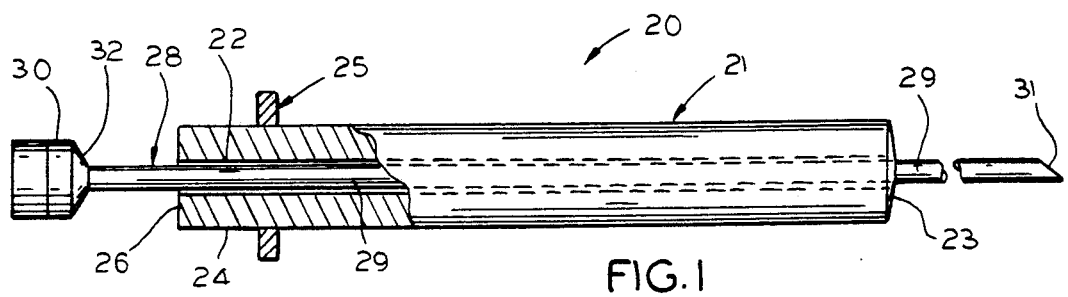
FIG. 1 of the drawings is an elevated plan view in partial cut-away, showing, in particular, the internal channel of the canulated shaft, as well as the slidable positioning of the shaft of the puncturing tool therewithin.

While this invention is susceptible of embodiment in many different forms, there is shown in the drawings, and will herein be described in detail, several specific embodiments with the understanding that the present disclosure is to be considered as a exemplification of the principles of the invention and is not intended to limit the invention to the embodiment illustrated.

Arthroscopy portal maker 20 is shown in FIG. 1, as including canulated shaft 21 and puncturing tool 28. Canulated shaft 21 includes internal channel 22, cutting end 23 and gripping portion 24 at blunt end 26 opposite the cutting end. Also proximate blunt end 26 is a preclusion means 25 that extends from gripping portion 24. Preferably, cutting end 23 of canulated shaft 21 has serrated edges, or alternatively, it is beveled at the end so as to facilitate cutting as well as ease in insertion. Internal channel 22 serves to facilitate slidable engagement with additional surgical tools, such as puncturing tool 28—which in this embodiment is a conventional spinal needle. Preferably, internal channel 22 has a cylindrical configuration.

Figure 2:
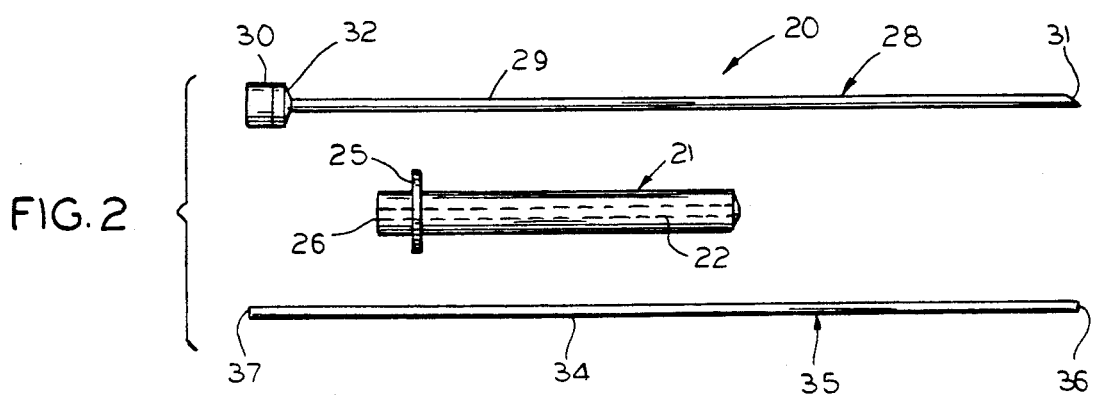
FIG. 2 of the drawings is an elevated side view of the arthroscopy portal maker showing, in particular, the puncturing tool, the canulated shaft and the blunt wire rod.

Puncturing tool 28 includes shaft 29, hub portion 30 and sharp point 31. Hub portion 30 has a bottom surface 32 adjacent shaft 29. As can be seen in FIG. 1, internal channel 22 of canulated shaft 21 has a diameter only slightly larger than the outer diameter of shaft 29 of puncturing tool 28 so as to facilitate slidable cooperation therebetween with a minimal amount of free play. FIG. 2 illustrates the relative lengths of canulated shaft 21 and puncturing tool 28. When puncturing tool 28 is initially slidably engaged within canulated shaft 21, hub portion 30 will be positioned proximate to blunt end 26 of canulated shaft 21, and sharp point 31 will be oriented in the direction of cutting end 23 of the shaft.

Arthroscopy portal maker 20, as is shown in FIG. 2, also includes puncturing tool 28, and wire rod 35. Wire rod 35 is blunt at both of its ends 36 and 37, and further includes shaft 34. As will be shown more fully in FIG. 3 and FIG. 6, internal channel 22 facilitates slidable cooperation with puncturing tool 28, as well as blunt wire rod 35.

Figure 3:
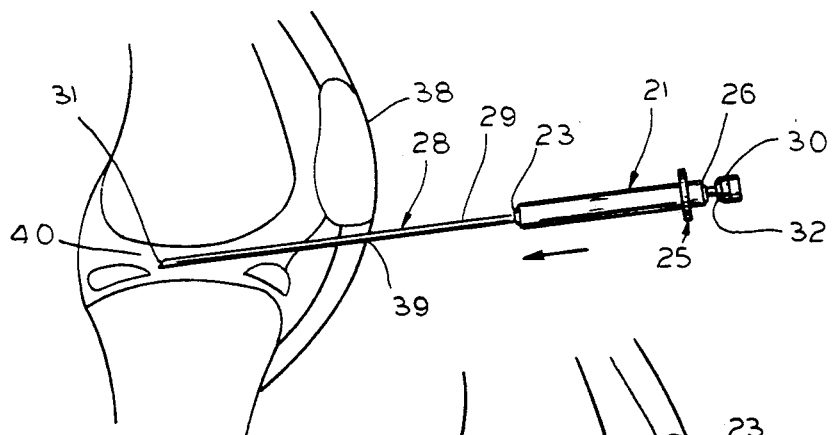
FIG. 3 of the drawings is an elevated side view of the canulated shaft and puncturing tool, in operation, after the puncturing tool has been inserted into the area where further surgical procedures are to be performed, and prior to the cutting end of the canulated shaft being inserted into the joint area.
Figure 4:
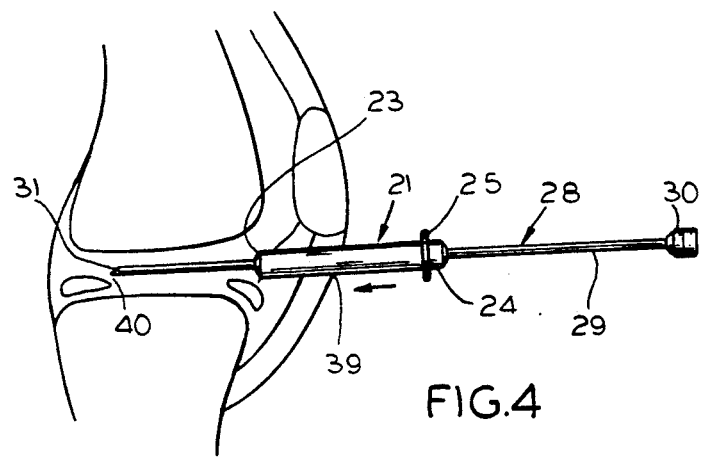
FIG. 4 is a side view of the canulated shaft and puncturing tool, in operation, after the cutting end of the canulated shaft has been inserted into the joint area.

Arthroscopy portal maker 20 is shown in FIG. 3 and FIG. 4, particularly showing the proper positioning of canulated shaft 21 over shaft 29 of puncturing tool 28, after sharp end 31 of puncturing tool 28 has pierced through the skin of a patient's joint 38 at puncture point 39, and after puncturing tool 28 has been pushed through the tissue to area 40 where further surgical procedures are to be performed. Once puncturing tool 28 is properly inserted, as well as prior to actually piercing the skin, canulated shaft 21 will be positioned so that blunt end 26 is maintained substantially proximate to bottom 32 of hub 30 of puncturing tool 28, and cutting end 23 of canulated shaft 21 is oriented toward joint 38.

Proper insertion of puncturing tool 28 is achieved by grasping hub 30 of puncturing tool 28 with one hand, and gripping portion 24 with the other hand, and then positioning sharp end 31 of puncturing tool 28 at desired point of entry, such as entry point 39, of joint 38. Preferably, the hand used in cooperation with gripping portion 24 will be partially wrapped around preclusion means 25 for bracing purposes while using the puncturing tool 28. After sharp point 31 of puncturing tool 28 is properly positioned at desired point of entry 39, the surgeon then forces puncturing tool 28, in the direction of the arrow, until sharp end 31 of puncturing tool 28 has pierced the skin and has been located to area 40 where further surgical procedures are to be performed. As can be seen, during the insertion of puncturing tool 28, as well as after it has been properly inserted, canulated shaft 21 is to be maintained proximate to bottom 32 of hub 30 of puncturing tool 28. After puncturing tool 28 is inserted into area 40 where further surgical procedures are to be performed, canulated shaft 21 must be slid in the direction of the arrow, along shaft 29 of spinal needle 28, so as to force cutting end 23 of canulated shaft past point of entry 39, and then through the tissue near the joint, until a substantial portion of canulated shaft 21 has been positioned therewithin, as shown in FIG. 4.

Figure 5:
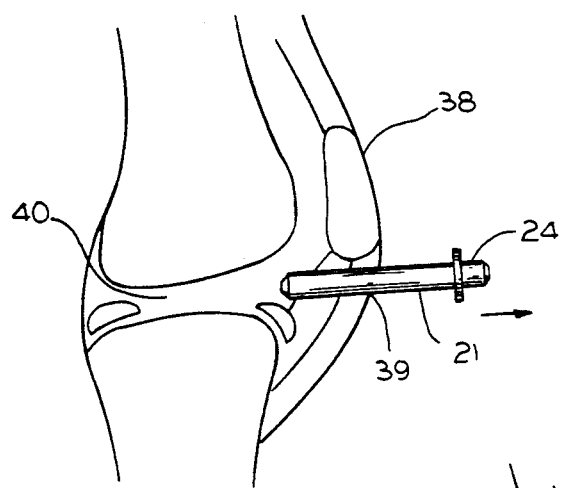
FIG. 5 of the drawings is a side view of the canulated shaft after it has been inserted into the joint area, and after the puncturing tool has been slidably removed therefrom.

Canulated shaft 21 is shown in FIG. 5, after the shaft has been properly inserted into joint area 38, and after puncturing tool 28 has been removed from area 40 where further surgical procedures are to be performed, as well as after puncturing tool 28 has been slidably removed from internal channel 22 of canulated shaft 21. Such slidable removal of puncturing tool 28 from canulated shaft 21 is accomplished by merely grasping gripping portion 24 with one hand, while pulling on hub 30 of spinal needle 28 with the other hand. Puncturing tool 28 is then pulled, in the direction of the arrow shown in FIG. 5, while maintaining canulated shaft 21 in place, until puncturing tool 28 is completely removed from canulated shaft 21.

Figure 6:
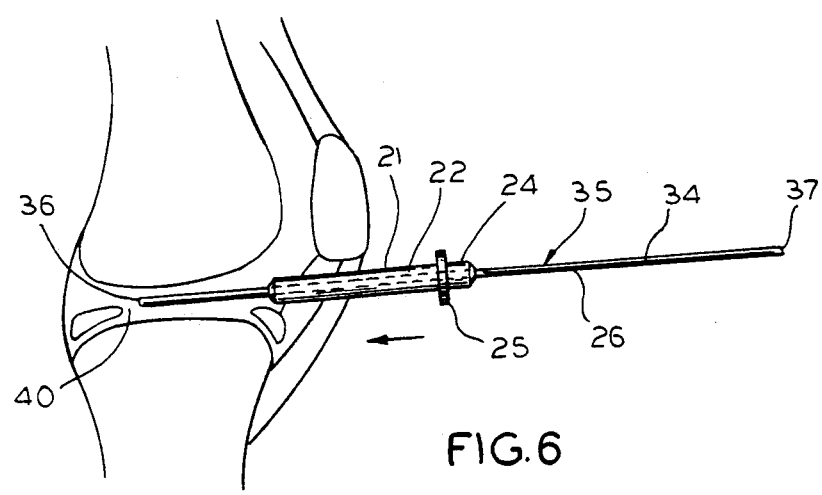
FIG. 6 of the drawings is a side view of the canulated shaft as well as the blunt wire rod, in operation, after the blunt wire rod has been inserted through the internal channel of the canulated shaft and into the area where further surgical procedures are to be performed within the joint.

After puncturing tool 28 has been completely removed from canulated shaft 21, blunt wire rod 35 is slidably inserted through blunt end 26 into internal channel 22 of canulated shaft 21, in the direction of the arrow, until insertion end 36 of wire rod 35 has been inserted through the hole previously made by puncturing tool 28 (as shown in FIG. 3), and accordingly forced toward the location previously occupied by puncturing tool 28, shown in FIG. 6.

If desired, blunt wire 35 may be inserted to the precise location that had previously been occupied by sharp end 31 of puncturing tool 28. Such insertion of wire rod 35 is achieved by grasping shaft 34 of blunt wire rod 35, near outer end 37, with one hand, and grasping gripping portion 24 of canulated shaft 21 with the other hand. As was recommended during the insertion of puncturing tool 28, it is also preferred during this procedure that the hand used to grasp gripping portion 24 of canulated shaft 21, be partially wrapped around preclusion means 25 so as to faciliate proper securing of canulated shaft 21, within joint area, during insertion of wire rod 35. Next, blunt wire rod 35 is inserted at blunt end 26 of canulated shaft 21 and into internal channel 22. Wire rod 35 is then pushed through internal channel 22 of canulated shaft 21.

Figure 7:
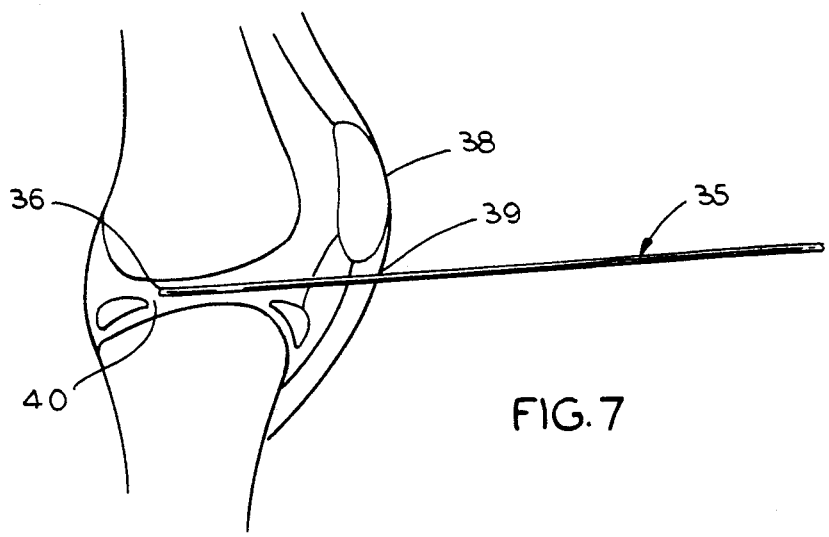
FIG. 7 of the drawings is a side view of the blunt wire rod within the joint area, and after the canulated shaft has been completely slidably removed from the joint area, as well as from the blunt wire rod.

After blunt wire rod 35 has been properly positioned in or near area 40 where further surgical procedures are to be performed, canulated shaft 21 is then slidably removed from blunt wire rod 35 and accordingly out and away from the area within the joint that canulated shaft 21 had occupied. The removal of canulated shaft 21 is accomplished by grasping shaft 39 of rod 35 near end 37, with one hand, and then simply pulling canulated shaft 21, by preclusion means 25, if desired, out and away from joint area 38. Such pulling of canulated shaft 21 is continued until it has been completely slidably removed over and past end 37 of wire rod 35, as shown in FIG. 7. When canulated shaft 21 is completely removed, blunt wire rod 35 will remain within joint area 38 at or near the precise location where further surgical procedures are to be performed.

Figure 8:
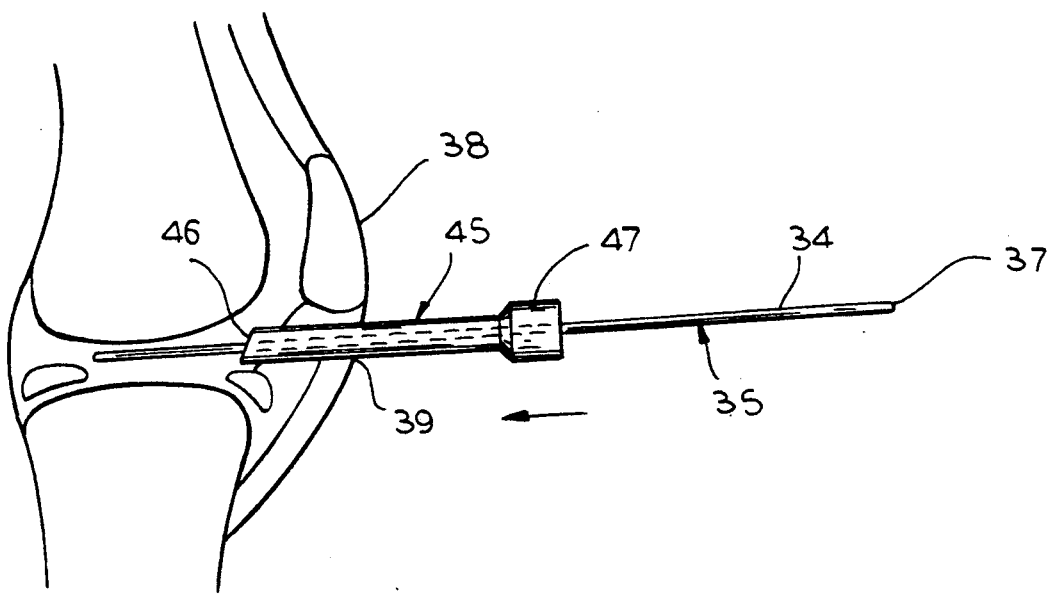
FIG. 8 of the drawings is a side view of a conventional canula after it has been slidably positioned over the blunt wire rod and into the joint area.

After canulated shaft 21 of arthroscopy portal maker 20 is removed from joint area 38, as shown in FIG. 7, a conventional canula 45, having a hub 47, and a non cutting end 46 is then slidably positioned over outer end 37 of shaft 34 of blunt wire rod 35. This canula 45 is then slid into the area which canulated shaft 21 had previously occupied. The proper positioning of conventional canula 45 is accomplished by grasping hub 47 of conventional canula 45 with one hand, while holding shaft 34 of blunt wire rod 35 with the other. Conventional canula 45 is then slid, in the direction of the arrow, as shown in FIG. 8, toward and past point of entry 39 until conventional canula 45 occupies substantially the same location as that previously occupied by canulated shaft 21. As the tissue was previously cut away by cutting end 23 of canulated shaft 21, a surgeon will easily be able to properly position conventional canula 45 into the previously occupied area. Additionally, because conventional canula 45 has a relatively blunt end 46, as opposed to a cutting end, such as cutting end 23 of canulated shaft 21 of arthroscopy portal maker 20, over-insertion of conventional canula 45 should not occur.

Figure 9:
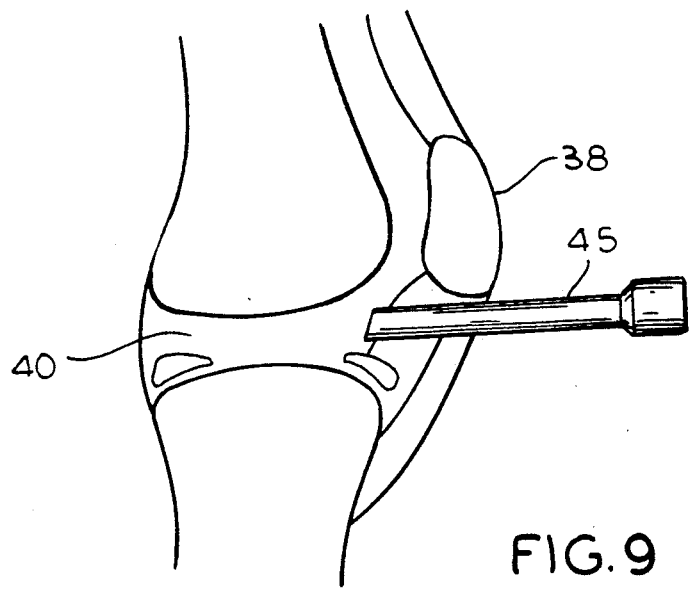
FIG. 9 of the drawings is a side view of the conventional canula, showing in particular, the maintained positioning of the conventional canula within the joint area, after the blunt wire rod has been completely removed.

After conventional canula 45 is properly inserted, blunt wire rod 35 is to be slidably removed from within the joint area, as well as slidably removed completely out and away from conventional canula 45. Removal of blunt wire rod 35 is achieved by simply grasping shaft 34 of blunt wire rod 35 with one hand, while holding on to hub portion 47 of conventional canula 45 with the other hand. Blunt wire rod 35 is then pulled out and away from within the joint area until it is completely removed from conventional canula 45 as shown in FIG. 9. Once completely removed, additional arthroscopic tools can be slidably inserted within conventional canula 45, and repositioned to the precise location 40 where further surgical procedures are to be performed.

Figure 10:
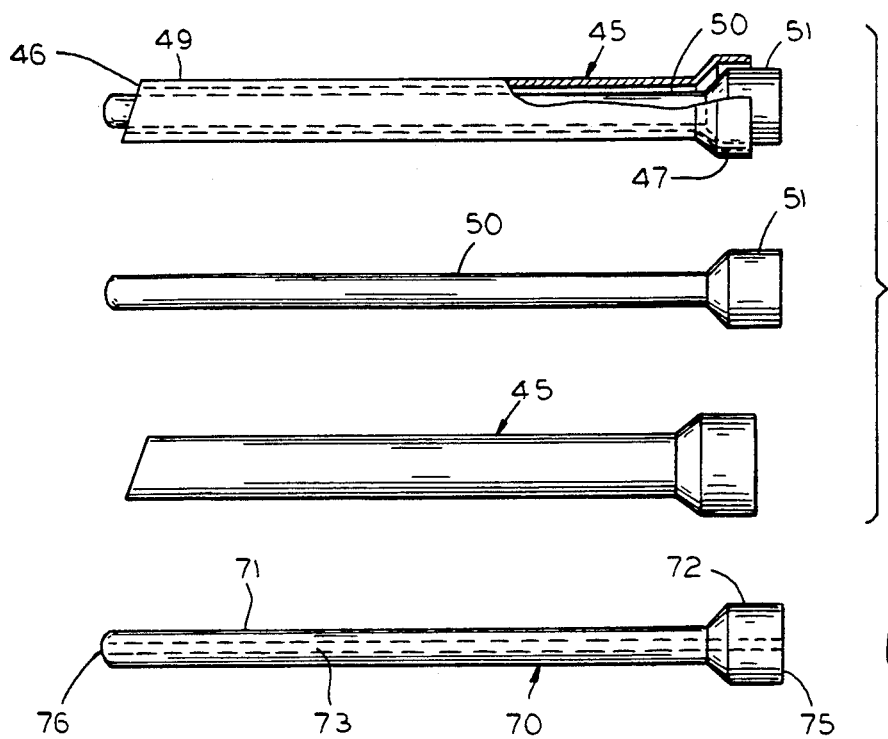
FIG. 10 of the drawings shows a prior art canula and obturator, as well as a partial cut-away view of the conventional canula, showing in particular, the slidable engagement of the obturator within the canula.

Conventional canula 45, along with conventional obturator 50, are shown in FIG. 10, as comprising prior art. As the prior art shows, obturator 50 slidably engages with internal channel 49 of conventional canula 45. Once inserted, obturator 50 occupies substantially all of internal channel 49 of conventional canula 45. Over insertion of obturator 50 within conventional canula 45 is eliminated as a result of hub 51 of obturator 50 having a larger diameter than the diameter of internal channel 49 of conventional canula 45. When completely inserted within conventional canula 45, hub 51 will abut with internal area of hub 47 of conventional canula 45. Since the obturator occupies substantially all of internal channel 49 of conventional canula 45, soft tissue will not clog internal channel 49 during the actual insertion into the patient.

Figure 11:
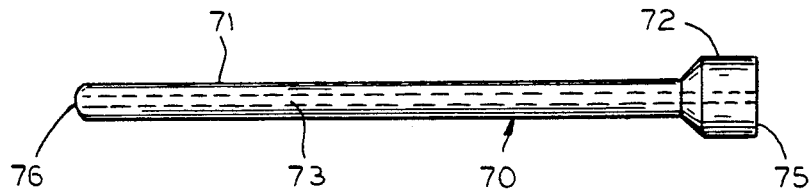
FIG. 11 of the drawings is an elevated side view of the canulated obturator, showing in particular, the internal channel of the obturator.
Figure 12:
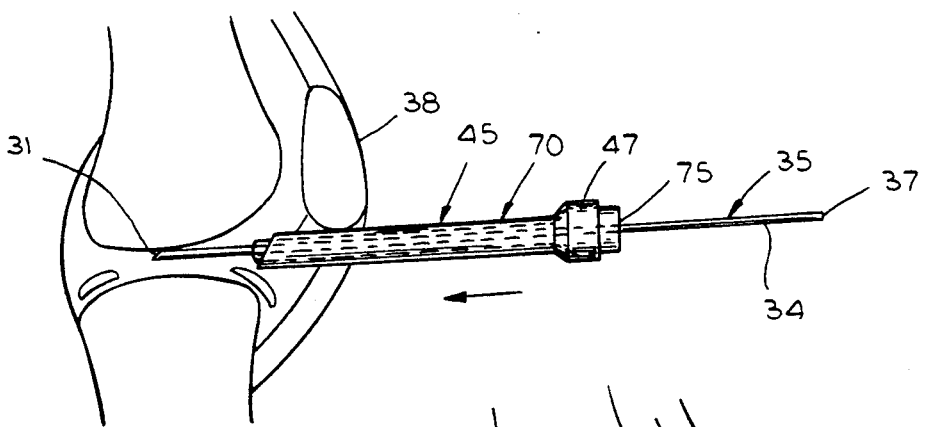
FIG. 12 of the drawings is an elevated side view of a conventional canula and the canulated obturator, in operation, showing in particular, the positioning of the canulated obturator within the conventional canula, as well as the slidable engagement of the canulated obturator over and around the blunt wire rod, after it has been inserted into the joint area.

Accordingly, as an additional embodiment of the invention, as well as an additional surgical procedure, a canulated obturator 70 is shown in FIG. 11 as including internal channel 73. Internal channel 73 has a first open end 76, and a second open end 75 at hub 72. Preferably internal channel 73 is cylindrical and has a diameter only slightly larger than the outer diameter of blunt wire rod 35 so as to closely conform to the rod. In operation, after canulated shaft 21 of arthroscopy portal maker 20 is removed from blunt wire rod 35, as shown in FIG. 7, a surgeon inserts canulated obturator 70 into internal chamber 49 of conventional canula 45 and then slides internal channel 73 of obturator 70 over blunt wire rod 35, in the direction of the arrow, until properly positioned within the joint area, as shown in FIG. 12. The use of such a canulated obturator 70, in cooperation with conventional canula 45, as well as blunt wire rod 35, facilitates easy insertion of canula during insertion into the joint area.

Figure 13:
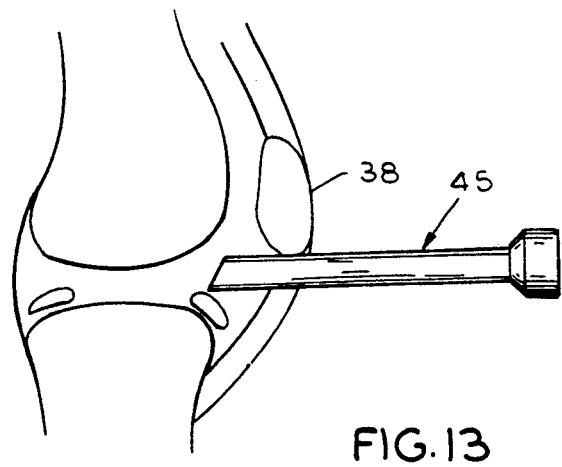
FIG. 13 of the drawings is an elevated side view of a conventional canula, within the joint area, after the blunt wire rod and canulated obturator have been completely removed.

After canulated obturator 70 and conventional canula 45 have been properly inserted within the joint area, canulated obturator 70, along with blunt wire rod 35 are slidably removed out and away from the internal area of the joint, as well as out and away from conventional canula 45, as shown in FIG. 13. Accordingly, additional surgical tools can then be inserted into conventional canula 45, and into the joint area, to the precise location previously occupied by blunt wire rod 35, as well as puncturing tool 28, as shown in FIG. 2 and FIG. 3.

Figure 14:
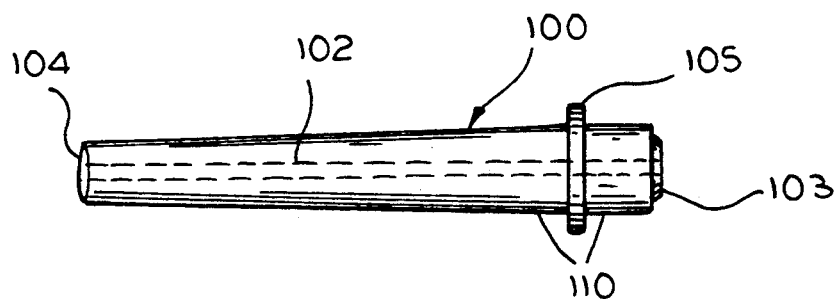
FIG. 14 of the drawings is an elevated side view of the canulated shaft, showing in particular, the preclusion means, and the increasingly larger diameter of the shaft from approximately the shaft's cutting end to approximately its gripping end.

Another embodiment shows canulated shaft 100 in FIG. 14, as including cutting end 104, blunt end 103, internal channel 102 and preclusion means 105. As can be seen, outer diameter of canulated shaft 100 is larger closer to preclusion means 105 than it is near cutting end 104. Such an increased outer diameter serves as an aid, along with preclusion means 105, to prevent over insertion of canulated shaft 100 within a patient's joint area. Also shown in FIG. 14 is gripping portion 110 of canulated shaft 100.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. A method for making a portal for arthroscopic surgery comprising the steps of:
   slidably positioning a canulated shaft, having a cutting portion and a gripping portion, over a puncturing tool of the type having a first sharp end and a second end, so as to locate said cutting portion of said canulated shaft proximate to said first sharp end of said puncturing tool;
   positioning said first sharp end of said puncturing tool at the location where said portal is to be made;
   puncturing said location where said portal is to be made with said first sharp end of said puncturing tool;
   pushing said puncturing tool through said puncture to an area where further surgical procedures are to be performed;
   sliding said cutting portion of said canulated shaft along said puncturing tool in the direction of said first sharp end of said puncturing tool;
   slidably removing said puncturing tool from said canulated shaft, and accordingly out from said area where said further surgical procedures are to be performed;
   inserting a rod through said canulated shaft and through said puncture caused by said puncturing tool;
   slidably removing said canulated shaft over said rod;
   slidably inserting a hollow tube over and around said rod until said hollow tube is positioned in substantially the same location which said canulated shaft had previously occupied; and
   slidably removing said rod from said hollow tube, and accordingly out and away from said area where said further surgical procedures are to be performed.

2. The method of claim 1 in which the step of slidably inserting a rod through said canulated shaft and through said puncture caused by said puncturing tool, further includes the step of slidably inserting said rod to substantially the precise location where said puncturing tool has previously occupied.

3. The method of claim 1 including the step of slidably inserting a canulated obturator into said hollow tube, prior to the step of slidably inserting a hollow tube over and around said rod.

* * * * *